United States Patent
Fujioka et al.

[11] Patent Number: 6,129,717
[45] Date of Patent: Oct. 10, 2000

[54] ABSORBENT ARTICLE AND METHOD FOR PRODUCING THE SAME

[75] Inventors: Yoshihisa Fujioka, Kagawa; Ichiro Wada, Ehime; Chimari Fujita, Ehime; Norihiko Ishikawa, Ehime, all of Japan

[73] Assignee: Uni-Charm Corporation, Ehime, Japan

[21] Appl. No.: 08/881,069

[22] Filed: Jun. 24, 1997

[30] Foreign Application Priority Data

Jul. 2, 1996 [JP] Japan ................................. 8-172528

[51] Int. Cl.$^7$ ................................................. A61F 13/15
[52] U.S. Cl. ..................... 604/368; 604/374; 604/375; 604/378; 604/379; 604/385.01
[58] Field of Search ..................... 604/368, 365, 604/378–380, 369, 384, 374–377, 385.01

[56] References Cited

U.S. PATENT DOCUMENTS

| | | | |
|---|---|---|---|
| H1511 | 12/1995 | Chappell et al. | 604/378 |
| Re. 32,957 | 6/1989 | Elias | 604/368 |
| 2,331,271 | 10/1943 | Gilchrist | 604/368 |
| 3,544,420 | 12/1970 | Murphy et al. | 604/379 |
| 4,055,180 | 10/1977 | Karami | 604/368 |
| 4,260,443 | 4/1981 | Lindsay et al. | 604/368 |
| 4,360,021 | 11/1982 | Stimer | 604/369 |
| 4,662,876 | 5/1987 | Weigner | 604/308 |
| 4,685,914 | 8/1987 | Holtman | 604/365 |
| 5,149,332 | 9/1992 | Walton et al. | 604/379 |
| 5,425,725 | 6/1995 | Tanzer et al. | 604/368 |
| 5,505,720 | 4/1996 | Walters et al. | 604/368 |
| 5,614,283 | 3/1997 | Potnis | 604/372 |
| 5,788,684 | 8/1998 | Abuto et al. | 604/368 |

FOREIGN PATENT DOCUMENTS

| | | | |
|---|---|---|---|
| 1492430 | 9/1970 | Germany | 604/378 |
| 2904634 | 8/1979 | Germany | 604/368 |
| 61-30041 | 7/1986 | Japan . | |
| 63-23078 | 6/1988 | Japan . | |
| 6-254118 | 9/1994 | Japan . | |
| 7-73591 | 8/1995 | Japan . | |
| 1315431 | 5/1973 | United Kingdom | 604/368 |

*Primary Examiner*—John G. Weiss
*Assistant Examiner*—K. M. Reichle
*Attorney, Agent, or Firm*—Koda & Androlia

[57] ABSTRACT

An absorbent article including an inner sheet and first and second outer sheets. The first outer sheet is of a fine interstice while the second outer sheet is fluid permeable. Through crepe processing, a great number of recesses are formed on an absorbent crepe sheet having wrinkles as the inner sheet. Highly absorbent polymers are charged in the recesses. Then, the first outer sheet adheres to the face on the opening side of the recesses of the inner sheet, while the second outer sheet adheres to the face of the opposite side of the inner sheet. The second outer sheet is positioned toward the side of fluid absorption. When a fluid is applied on the absorbent article, the fluid passes through the second outer sheet onto the inner sheet and the highly absorbent polymers. Because the crepe wrinkles are elongated and extended when the inner sheet absorbs fluid, the recesses are enlarged.

4 Claims, 3 Drawing Sheets

ABSORBENT ARTICLE AND METHOD FOR PRODUCING THE SAME

BACKGROUND OF THE INVENTION

1. Field of the Invention

The present invention relates to an absorbent article for use in disposable diapers and sanitary napkins; more specifically, the present invention relates to a highly absorbable absorbent article of a slim type and a method for producing the same.

2. Description of the Prior Art

In disposable diapers and sanitary napkins, an absorbent article is interposed between a back sheet comprising a fluid-impermeable resin sheet and an inner sheet in direct touch with the skin of a wearer. As the absorbent article, generally, use is made of a mixture of ground pulp and a highly absorbable resin (so-called super absorbent polymers; abbreviated as SAP) such as polyacrylic acid, which mixture is interposed between an upper sheet and a lower sheet, both comprising a thin paper. Because SAP are more highly absorbable than pulp, the absorbent article is superior to an absorbent article where only pulp is interposed between the upper sheet and the lower sheet, in terms of fluid absorptivity. Thus, the absorbent article can be made thin. Additionally because SAP swell after fluid absorption and are then solidified in the form of gel, SAP can securely retain absorbed urine and blood of menstruation inside the absorbent article, to thereby prevent the absorbed fluid from leaking from the article. Furthermore, SAP are a powder (granules) in their dry state, while SAP turn into a gel after fluid absorption. Therefore, an absorbent article with SAP interposed between the upper and lower sheets therein is soft, compared with an absorbent article with only pulp interposed between the upper and lower sheets therefore the absorbent article with SAP can readily be deformed along with the body shape of a wearer. Thus, diapers and sanitary napkins using the absorbent article confer good feeling on wearing.

When the amount of SAP to pulp is increased so as to enhance the absorptivity, the SAP powder in its dry state before fluid absorption moves between the upper and lower sheets when the wearer makes a motion. As result, the SAP distribution may be non-uniform in the absorbent article. When a part with less SAP absorb urine or blood of menstruation, accordingly, the overall absorption effect of the absorbent article is reduced. Additionally, SAP modified into a gel after fluid absorption (after absorbing fluid) moves between the upper and lower sheets, so that the SAP eventually may be gathered and turned into a solid mass and the resulting mass may break the upper and lower sheets resulting in a unpleasant feeling to the wearer.

So as to overcome the problems described above, for example, Japanese Patent Publication No.61-30041, Japanese Patent Provisional Publication No.6-254118, Japanese Patent Publication No.7-73591 and Japanese Utility Model Publication No.63-23078 describe an absorbent article wherein a given amount of a highly absorbable substance is placed at intervals on a sheet whereby the highly absorbable substance is uniformly dispersed on the whole surface of the sheet and a cover sheet with recesses and protrusions formed thereon covers and bonded to the sheet.

In such an absorbent article, the highly absorbable substance is dispersed at a given amount and pressed with the cover sheet to retain the given amount of the highly absorbable substance with no movement from the initial positions. Thus, the transfer of the highly absorbable substance in the absorbent article can be prevented. Furthermore, the thickness of the absorbent article can be made constant. Still, the fluid absorption in volume of the whole absorbent article can be elevated.

When covering the sheet placing the highly absorbable substance thereon with a cover sheet, however, the positioning should be done so as to securely place the highly absorbable substance in the recesses of the cover sheet. Thus, the production of such absorbent article is laborious. So as to secure a large space in which the highly absorbable substance swells, it is required that the depth and diameter of the recesses of the cover sheet should be so enlarged that the volume of each of the recesses is larger than the volume of the given amount of the highly absorbable substance. Hence, the dimension of the thickness of the absorbent article is larger, which limits the slimming of the absorbent article. When the volume of each of the recesses in the cover sheet is small so as to make the absorbent article slim, alternatively, the cover sheet suppresses the swelling of the highly absorbable substance on fluid absorption, causing a reduction in the absorptivity.

The present invention can overcome the conventional problems. It is an object of the present invention to provide a highly absorbable absorbent article of a slim type, capable of preventing the transfer of the highly absorbable substance in the absorbent article and preventing the thickening of the absorbent article by making a space for the highly absorbable substance after fluid absorption to sufficiently swell in the sheets; and a method for producing the same.

SUMMARY OF THE INVENTION

The absorbent article of the present invention comprises an inner sheet interposed between two outer sheets, the inner sheet being bonded to the outer sheets.

The inner sheet is a fluid-absorbable crepe sheet with a great number of recesses formed thereon. The fluid-absorbable crepe sheet is produced by subjecting a fluid-absorbable sheet such as rayon paper or pulp paper to crepe processing to form a great number of fine wrinkles thereon. Then, by holding the crepe sheet with a roller with recesses and protrusions on the surface, a great number of recesses are molded independently on the whole surface of the crepe sheet.

Absorbent polymers are charged in the recesses. The absorbent polymers swell on water absorption. The absorbent polymers include highly water-absorbable resin (referred to as "super absorbent polymers"; abbreviated as "SAP") of starches, celluloses and synthetic polymers and the like. The SAP have great water absorptivity and high water retention. The SAP of the synthetic polymers include those of polyacrylates, polyvinyl alcohols, polyacrylamides, polyoxyethylenes and the like. A variety of these resins are used as such absorbent polymers. Other than the SAP, water-insoluble hydrogels are used additionally. Together with the absorbent polymers, other absorbent materials such as ground pulp may be charged satisfactorily. At least one of the two outer sheets should be a fluid-permeable sheet. One outer sheet of the two outer sheets should be overlaid on the inner sheet, so as to occlude the side of the openings of the recesses charged with the absorbent polymers on the inner sheet, while the other outer sheet is overlaid on the face opposite to the face where the one outer sheet is overlaid on the inner sheet.

When urine or blood of menstruation is spotted on the absorbent article, the crepe wrinkles on the inner sheet are smoothed and enlarged while the absorbent polymers such as SAP in the recesses absorb the fluid to swell. Because a space is formed between the recesses adjacent to each other on the inner sheet, each recess swells toward the space between the recess and the adjacent recess when absorbent polymers swell in the recesses.

At least one of the two outer sheets is a fluid-permeable sheet, for example, rayon sheet or rayon spun-lace. The fluid-permeable sheet is then positioned toward the receiving side of urine and blood of menstruation, namely the side comprising a fluid-permeable top sheet. In contrast, the other outer sheet is positioned toward the non-receiving side of urine and blood of menstruation, namely the side comprising a fluid-impermeable back sheet. The other outer sheet is not necessarily a fluid-permeable sheet. If the two outer sheets are fluid-permeable sheets, any face of the absorbent article may satisfactorily be positioned toward the receiving side of urine and blood of menstruation.

The method for producing the absorbent article comprises a step of molding a great number of recesses on a fluid-absorbable crepe sheet under pressure thereby forming an inner sheet, a step of charging absorbent polymers or a combination of absorbent polymers with additional absorbent materials in the recesses on the inner sheet, a step of bonding the one outer sheet to the inner sheet, so as to occlude the side of the opening of the recesses charged with the absorbent polymers or the combination of the absorbent polymers with the additional absorbent materials, and a step of bonding the other outer sheet to the face of the inner sheet on the opposite side of the face where the one outer sheet is overlaid on the inner sheet, after the process of forming the inner sheet.

By the method for producing the absorbent article, preferably, the inner sheet is bonded to the one outer sheet or the inner sheet is bonded to the other outer sheet, by means of adhesion with an insoluble adhesive means. The insoluble adhesive means includes adhesion with a hot-melt adhesive. The hot-melt adhesive includes for example olefin adhesives such as polyethylene or polypropylene; and adhesives of ethylene vinyl alcohols (EVA series). For adhesion with the hot-melt adhesive, the hot-melt adhesive is coated in a spiral shape on the bonding faces of one and the other outer sheets. Then, the individual outer sheets are overlaid on the inner sheet so that the faces coated with the adhesive are positioned toward the inner sheet, for adhesion of the outer sheets to the inner sheet for bonding them together.

Besides, by interweaving polyethylene (PE) or polypropylene (PP) into the inner sheet and one and the other outer sheets and overlaying these sheets together, followed by heating to melt the polypropylene or polyethylene thereby melt bonding the individual sheets, these sheets are bonded together. By adhesion of the inner sheet to one outer sheet or adhesion of the inner sheet to the other outer sheet by means of a fluid-insoluble adhesive means, thereby bonding them together, the bonding strength between the individual sheets on fluid absorption can be maintained high.

As has been described above, the one outer sheet and the other outer sheet are rayon paper or rayon spun-lace. When the outer sheet bonded to the side of the openings of the recesses on the inner sheet is a fine paper or fine non-woven fabric, the absorbent polymers in the recesses are hardly poured out of the recesses outwardly. Otherwise, the outer sheet bonded to the side of the openings of the recesses may satisfactorily comprise a non-woven fabric interwoven with polyethylene or polypropylene, to which heat and pressure are preliminarily applied to melt the interwoven PE or PP to make the interstice in between fibers close to make the fabric dense. In this case, the outer sheet bonded to the bottom side of the recesses on the inner sheet preferably comprises a fluid-permeable paper or nonwoven fabric, with a relatively crude, and the outer sheet is preferably used positioned toward the receiving side of urine and blood of menstruation.

The absorbent article of the present invention is filled in disposable diapers and sanitary napkins for use as an absorbent article. When the absorbent article of the present invention is filled in disposable diapers and sanitary napkins, a fluid-impermeable resin sheet is overlaid as a back sheet on the outer side of one outer sheet, while a top sheet directly in touch with skin is overlaid on the outer side of the other outer sheet.

Spotting urine or blood of menstruation on the absorbent article, these fluids pass through the top sheet and then through the outer sheet to be absorbed in the inner sheet. The absorbent polymers charged in the recesses on the inner sheet, such as SAP, absorb the fluids to swell and turn gel. Because the inner sheet with the absorbent-polymer-placing recesses formed thereon is an absorbable crepe sheet, the crepe wrinkles are extended (reversed) in the recesses on the inner sheet, immediately when the absorbent polymers such as SAP swell. Therefore, the swelling of SAP is not suppressed, which enable sufficient exertion of the fluid absorbing function of the absorbent polymers. If space (ii) is preliminarily formed between the adjacent recesses as shown in FIG. 2(A), in particular, the space (ii) allows the swelling of the recesses so that the recesses extensively swell. Thus, even if the fluid absorption increases in volume, the interval between the one outer sheet and the other outer sheet is not so enlarged, with the result that the overall dimension of the thickness of the absorbent article is not so enlarged even after fluid absorption.

As has been described above, the recesses on the inner sheet can swell, due to fluid absorption, toward the space between the one outer sheet and the other outer sheet. The volume of each of the recesses is satisfactorily of a size to charge absorbent polymers such as SAP powders or absorbent polymers and another absorbent materials, both at their dry state. In other words, a space to allow the swelling of absorbent polymers such as SAP as in the prior art is not any more necessarily arranged in the recesses charged with the absorbent polymers on the sheet, so the depth of the recesses can be made shallow. Absorbent polymers or absorbent polymers in combination with other absorbent materials can be placed more in the recesses; for example, absorbent polymers or absorbent polymers with another absorbent materials can be placed in the recesses even if these polymers charged therein occupy 70% or more of the volume of each of the recesses. Hence, the absorbent article can entirely be made highly absorbable of a slim type.

So as to allow the swelling of absorbent polymers such as SAP charged in the recesses, the ratio of the extensibility (crepe ratio) of the inner sheet produced by crepe processing is preferably 5% or more to 65% or less. The "crepe ratio" is represented by the formula $[(\Delta X—X)/X] \times 100$ (%), provided that X represents the length of the absorbent sheet after crepe processing; and $\Delta X$ represents the size of the absorbent sheet after extension due to water absorption.

The recesses are preferably formed at a ratio of 2 or more recesses/cm$^2$ to 13 recesses or less /cm$^2$. In this case, the absorbent article can be made thin, and more absorbent polymers can be charged in the recesses.

As shown in FIG. 2(A), one outer sheet is bonded between the openings of the adjacent recesses on the inner sheet, while the other outer sheet is bonded to the bottom side of the recesses. Because the inner sheet is bonded to the one outer sheet and the other outer sheet at the periphery of the openings of the recesses and on the bottom side of the recesses in such manner, the absorbent polymers or the absorbent polymers together with the additional absorbent materials are securely retained inside the recesses, whereby the transfer of the absorbent polymers or the absorbent polymers along the additional absorbent materials can be prevented. As shown in FIG. 2(A), additionally, region (ii) for allowing the swelling of the recesses can be procured between the one outer sheet and the other outer sheet. Thus, the absorbent polymers or the absorbent polymers together with the additional absorbent materials can be dispersed uniformly in the absorbent article, with no consequent reduction of the absorptivity of the absorbent article or with no consequent transfer or gathering of the gel-like mass of the absorbent polymers such as SAP, which mass is formed through fluid absorption, so that the absorbent article can swell. Accordingly, fluid can be absorbed uniformly into the absorbent polymers or the absorbent polymers together with the additional absorbent materials, and furthermore, the resulting sheet after absorption will not be thickened very much.

As has been described above, in accordance with the present invention, absorbent polymers or absorbent polymers together with an additional absorbent materials can be dispersed uniformly in the absorbent article and the space inside each of the recesses can be enlarged in response to the swelling of the absorbent polymers. Thus, a highly absorbable absorbent article of a slim type can be provided.

DETAILED DESCRIPTION OF THE PREFERRED EMBODIMENTS

Figure 1:
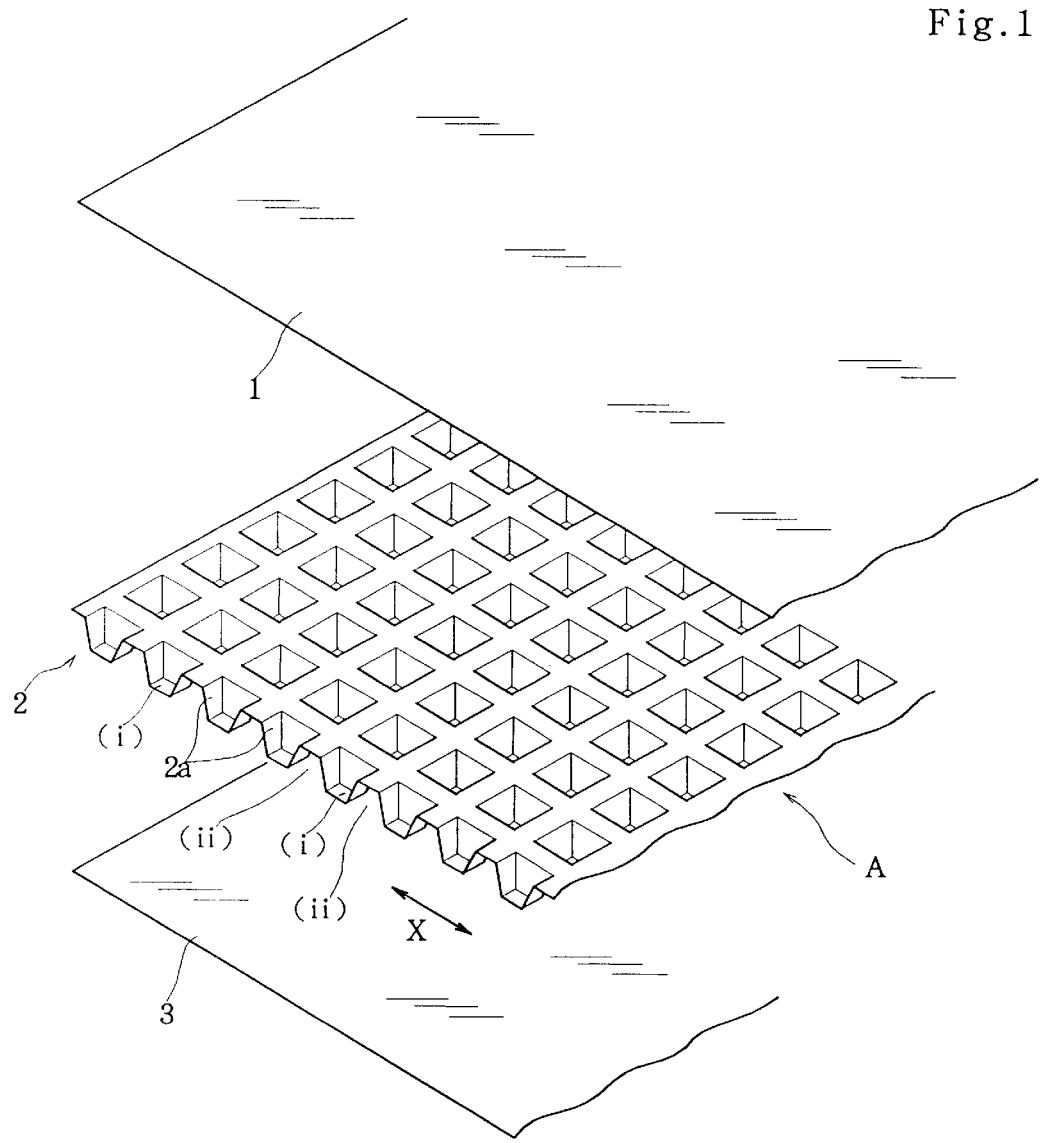
FIG. 1 is an exploded perspective view depicting the absorbent article in accordance with the present invention.
Figure 2:
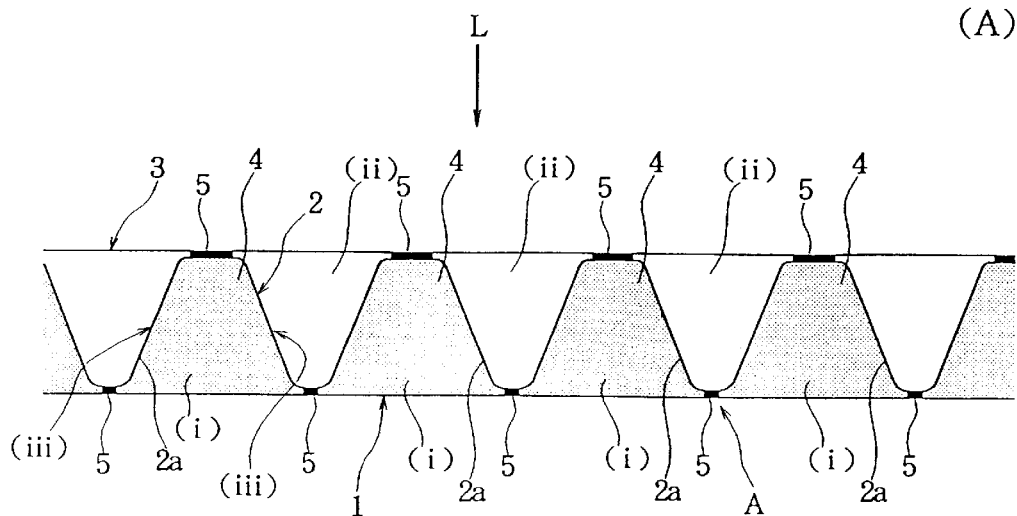
FIG. 2(A) is a cross-sectional view depicting the absorbent article before fluid absorption.
FIG. 2(B) is a cross-sectional view depicting the absorbent article after fluid absorption.
Figure 2:
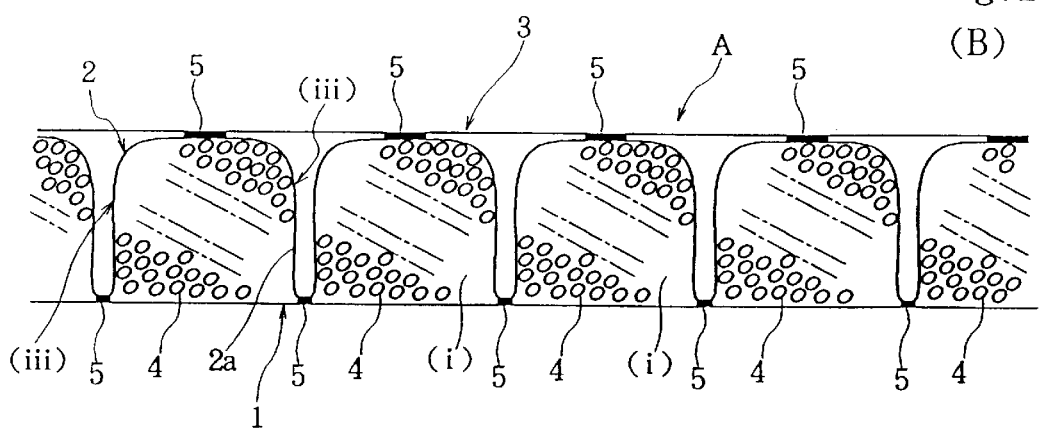

Absorbent article A shown in FIG. 1 is of a three-layer structure wherein inner sheet 2 is interposed between one outer sheet 1 and the other outer sheet 3. In FIG. 1, one outer sheet 1 is positioned upwardly, but when the absorbent article is arranged in a diaper or sanitary napkin, practically, one outer sheet 1 is positioned downwardly, while the other outer sheet 3 is positioned upwardly, as shown in FIGS. 2(A) and (B). Then, the other outer sheet 3 is positioned toward the side of receiving urine and blood of menstruation.

The one outer sheet 1 and the other outer sheet 3 are fluid-permeable rayon paper or fluid-permeable pulp paper or a non-woven fabric such as spun-lace formed from rayon. The base weight of the one outer sheet 1 and the other outer sheet 3 is 15 g/m² or more to 25 g/m² or less.

On Inner sheet 2, a great number of micro-fine wrinkles were formed along the direction vertical to the lengthwise direction (x direction) of the sheet, by subjecting an absorbent sheet such as rayon paper or pulp paper to crepe processing. The base weight of the absorbent sheet before crepe processing is 15 g/m² or more to 25 g/m² or less. When the absorbent sheet absorbs fluid, the microfine wrinkles get loose and extended, so that the absorbent sheet is smoothed out in the x direction. On the inner sheet 2, a great number of recesses 2a are formed. The recesses 2a are molded under pressure against a great number of recesses and protrusions in engagement to each other, which are preliminarily formed on the surface of a pair of rollers holding the absorbent sheet.

As shown in FIGS. 2(A) and (B), absorbent polymers are charged inside a plurality of the recesses 2a. As such absorbent polymer, primarily, SAP4 are charged therein. The SAP4 are a highly absorbable polymers, in powders or in granules at dry state, but on fluid absorption, the SAP4 swell into a gel. As the SAP, mainly, a polymers of polyacrylates can be used. Other than the SAP4, additional absorbent materials such as ground pulp can be mixed with the SAP and then charged in the recesses 2a.

Hot-melt adhesive 5 is coated on the bonding faces of the one outer sheet 1 and the other outer sheet 3, and between the two outer sheets is interposed the inner sheet 2, whereby the inner sheet 2 is bonded to the one outer sheet 1, and the inner sheet 2 is bonded to the other outer sheet 3. The hot-melt adhesive 5 is an insoluble adhesive of polyolefins such as polyethylene (PE) and polypropylene (PP) or of EVAs.

As shown in FIG. 2(A), in the absorbent article A, the one outer sheet 1 adheres to and is bonded to the periphery of the openings of the recesses 2a of the inner sheet 2 and the other outer sheet 3 adheres to and is bonded to the bottom side of the recesses 2a. Consequently, the side of the openings of the recesses 2a is closed with the one outer sheet 1. Then, a bag-like absorption region (i) is prepared with the recesses 2a and the one outer sheet 1, and the SAP4 are sealed in the absorption region (i). When a diaper or sanitary napkin using the absorbent article is worn, the SAP4 do not move inside the absorbent article A even if the wearer makes a motion.

Because the SAP4 are charged in the limited space as the absorbent region (i) and are therefore divided at a given amount in the absorbent article A and additionally because the given amount of the SAP4 is uniformly dispersed therein, the absorbent article A can procure the fluid absorbing function uniformly over a wide region thereof. Because the individual sheets are bonded together by means of the insoluble hot-melt adhesive 5, the adhesive strength of the bonded parts is not deteriorated even if fluid is spotted thereon. Thus, the three sheets are never separated from each other after fluid absorption, whereby the transfer of the SAP4 in the absorbent article A can be prevented. Because the SAP4 are divided and charged at an appropriate amount in each of the absorbent region (i), furthermore, a given divided amount of the SAP4 is solidified when the SAP4 absorb fluid, with no formation of an excessively large mass of the SAP4. Thus, it never occurs that the individual sheets are peeled off from each other due to the presence of such excessively large mass or that the sheets are broken, and therefore, the wearer never feels any unpleasant touch. Alternatively, one outer sheet 1, inner sheet 2 and the other outer sheet 3 are individually interwoven with PE or PP resin or the like, to bond the individual sheets together by hot melting.

As shown in FIG. 2(A), furthermore, in the absorbent region (i) charged with the SAP4, namely in between the adjacent recesses 2a on the inner sheet 2 between the one outer sheet 1 and the other outer sheet 3, space (ii) is formed where the one outer sheet 1 never adheres to the other outer sheet 3. When the fluid-absorbing SAP4 swells and the crepe wrinkles of the inner sheet 2 are smoothed out to expand the absorbent region (i), the volume of the space (ii) decreases thereby allowing the expansion.

The absorbent article A is produced by the method described below.

A great number of recesses 2a are molded under pressure on an absorbent sheet (with crepe) through crepe processing, to form inner sheet 2. Then, powdery or granule SAP4 is charged inside each of the recesses 2a, namely the bag-like absorbent region (i). Subsequently, one outer sheet 1 is overlaid over and adheres and is bonded to the opening side of the recesses 2a by means of hot-melt adhesive 5. At a process following the formation of the inner sheet 2, the other outer sheet 3 is overlaid over and adheres and is bonded to the bottom side of the recesses 2a on the inner sheet 2, by means of the hot-melt adhesive 5. For the bonding of the individual sheets, the hot-melt adhesive 5 is coated in a spiral shape on the faces of the one outer sheet 1 and the other outer sheet 3 to be bonded to the inner sheet 2. After overlaying the one outer sheet 1 and the other outer sheet 3 over the inner sheet 2, subsequently, the adhesive is dried under heating, by means of a heat roll for completion of the bonding.

Because fluid is spotted from the side of the other outer sheet 3 on the absorbent article A, a highly fluid-permeable sheet such as coarse paper or coarse non-woven fabric is used as the other outer sheet 3, so as to permeate fluid through the sheet. As one outer sheet 1, alternatively, use is made of a fine paper or fine non-woven fabric, in order that SAP4 at dry state prior to fluid absorption might not be leaked out of the recesses 2a outwardly. Additionally, the one outer sheet 1 is not necessarily a fluid-permeable sheet. Because the degree of the interstice of the one outer sheet 1 is different from that of the other outer sheet 3, as has been described above, two types of paper or non-woven fabric with coarse and fine interstices in between fibers should be used. Otherwise, when PE or PP is interwoven into the inner sheet 2 and the one outer sheet 1 and the other outer sheet 3, both comprising the same non-woven sheet, to bond these sheet together by hot melting, heat and pressure are applied to the one outer sheet 1 by means of a heat roll during hot melting to melt the PE or PP in the non-woven fabric, to thereby close the interstices in between fibers.

Figure 3:
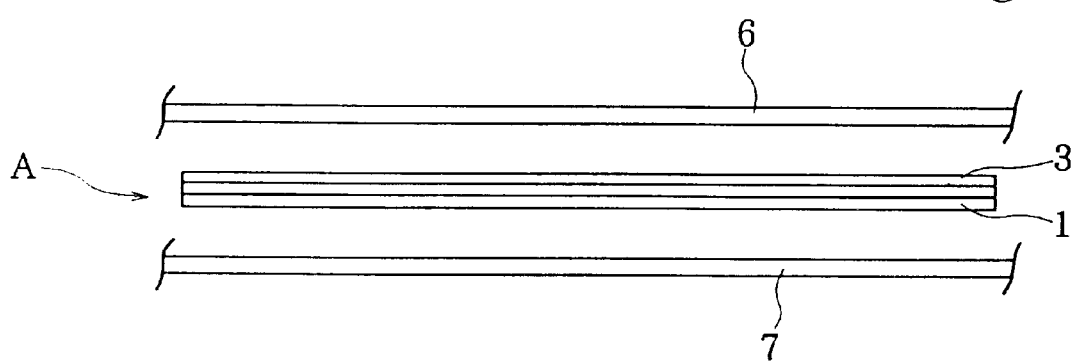
FIG. 3 is an exploded cross-sectional view of the absorbent article in accordance with the present invention interposed between a top sheet and back sheet of for example a diaper.

After the absorbent article A is formed by bonding the one outer sheet 1 and the other outer sheet 3 to the inner sheet 2, pattern multiple-weaving and cutting by means of cutter blade or water jet or the like are conducted, to cut the absorbent article A into a given shape following the shape of a disposable diaper or a sanitary napkin. As shown in FIG. 3, then, the other outer sheet 3 is positioned toward the side of receiving fluid such as urine and blood of menstruation, namely the side of top sheet 6 directly in contact to the skin of a wearer, while the one outer sheet 1 is positioned toward the side of fluid-impermeable back sheet 7, so that the absorbent article A is interposed between the back sheet 7 and the top sheet 6.

When a disposable diaper or a sanitary napkin arranged with the absorbent article A is worn on the body of a wearer, fluid such as urine or blood of menstruation is spotted from the side shown by L in FIG. 2(A). The fluid firstly permeates through the top sheet of the disposable diaper or the sanitary napkin and then through the other outer sheet 3 of the absorbent article A, to be absorbed into the absorbent sheet composing the inner sheet 2 and into the SAP4. The SAP4 absorbs the fluid and then swells and turns gel. After fluid absorption, the wrinkles made by crepe processing on the inner sheet 2 are extended (reversed). Thus, the volume of the absorbent region (i) in each of the recesses 2a is enlarged and concurrently, the SAP4 can swell following the extension of the inner wall of each of the recesses 2a. Because the opening side and bottom side of each of the recesses 2a are preliminarily bonded to the one outer sheet 1 and the other outer sheet 3, respectively, by means of insoluble hot-melt adhesive 5, the crepe wrinkles present at a part of the inner sheet 2 coated with the adhesive 5 are not smoothed out, while such crepe wrinkles are relatively freely smoothed out at the peripheral wall part (iii) of each of the recesses 2a. As shown in FIG. 2(B), therefore, each of the recesses 2a (bag-like absorbent region (i)) expands toward the space (ii) via the swelling of the SAP4. The peripheral wall part (iii) can freely expand in the space (ii), but the crepe wrinkles of the inner sheet 2 are scarcely smoothed out at the part bonded with the insoluble adhesive 5. Hence, the absorbent article A does not expand so much toward the direction, of the sheet thickness when the SAP4 swell, and ever after fluid absorption, the sheet can maintain the status-of such slim type.

The degree of the expansion of the absorbent region (i) varies, depending on the ratio of formed crepe, but if the degree of extensibility (crepe ratio) of the sheet through the extension of crepe wrinkles is below 5%, the enlargement of each of the recesses 2a is suppressed, whereby sufficient absorptivity cannot be attained. If the crepe ratio is above 65%, alternatively, the recesses 2a are so extensively enlarged that the ratio of the area bonded by means of the fluid-insoluble adhesive 5 to the whole area of the inner sheet 2 is too much reduced, causing the deterioration of the overall strength of the absorbent article A. If the crepe ratio is above 65%, the absorbent region (i) expands not only in the space (ii) but also expands distinctively toward the direction of the sheet thickness. After fluid absorption, the dimension of the thickness of the absorbent article A is therefore enlarged beyond necessary level. Thus, the inner sheet 2 is preferably crepe processed so that the crepe ratio are 5% or more to 65% or less.

By general crepe processing, furthermore, the absorbent sheet is processed so that the resulting wrinkles might be extended toward a direction vertical to the lengthwise direction (x direction). When crepe processing is conducted to form wrinkles toward two directions, namely a direction vertical to the lengthwise direction (x direction) and the lengthwise direction of itself, thereby crossing these wrinkles over each other, the recesses 2a can be extended toward any direction in the inner sheet 2, so that the SAP4 can consequently swell more readily.

The recesses 2a can expand in response to the swelling of the SAP4, due to the smoothing (reversion) of the micro-fine wrinkles formed by crepe processing. At the dry state prior to fluid absorption, thus, not any space should necessarily be procured in which the SAP4 swells in the recesses 2a. Hence, it is possible to charge the SAP4 of a volume occupying 70% or more of the volume of each of the recesses 2a. Additionally, the fluid absorption in volume per unit area of the absorbent article A can be set, depending on the number of the recesses 2a and the depth of each thereof. In order that the absorbent article A can be made of sufficiently absorb fluid such as urine and blood of menstruation, the recesses 2a are preferably formed at a ratio of 2 recesses/cm$^2$ or more to 13 recesses/cm$^2$ or less.

The dimension of two sides, namely lengthwise and crosswise sides of each of the recesses 2a is 3 to 5 mm, and by setting the depth of each of the recesses 2a at about 1 to 3 mm, fluid can be sufficiently absorbed into the SAP4 in the recesses but the dimension of the thickness of the overall absorbent article is not enlarged very much.

In the absorbent article of the present invention, as has been described in detail insofar, the SAP4 is charged into the recesses 2a formed on the overall surface of the inner sheet 2. Therefore, the SAP4 can uniformly be dispersed over the absorbent article A. Further, the recesses 2a expand on fluid absorption, to allow the swelling of the SAP4. Still further, a region for each of the recesses to expand is formed in between the inner sheet 2 and the one outer sheet 1 and in between the inner sheet and the other outer sheet 3. Thus, the absorption property of absorbent polymers can be exerted satisfactorily so that a highly absorbable absorbent article can be attained.

What is claimed is:

1. An absorbent article comprising:

a first outer sheet;

a second outer sheet being fluid permeable;

a fluid absorbent inner sheet made of an absorbent crepe paper having wrinkles capable of extending on fluid absorption between the first outer sheet and the second outer sheet, a plurality of recesses being formed on the inner sheet so that the inner sheet is composed of bottom portions of said recesses, wall portions of the recesses and a remaining portion excluding the recesses, said absorbent crepe paper having a crepe ratio of 5–65% and wherein the inner sheet is bonded to the first outer sheet at the remaining portion with an insoluble adhesive, thereby closing the recesses with the first outer sheet to form a plurality of absorbent regions between the first outer sheet and the inner sheet, and bonded to the second outer sheet at the bottom portions with an insoluble adhesive, thereby forming spaces between the second outer sheet and the inner sheet adjacent said recesses; and absorbent polymers capable of swelling on fluid absorption or absorbent materials together with the absorbent polymers charged in the recesses of the inner sheet whereby upon fluid absorption, the wall portions of said recesses expand while a thickness between the first outer sheet and the second outer sheet does not significantly expand and the absorbent regions expand toward the spaces.

2. An absorbent article according to claim 1, wherein the recesses are formed at a ratio of 2 recesses/cm$^2$ or more to 13 recesses/cm$^2$ or less on the inner sheet.

3. An absorbent article according to claim 1, wherein the first outer sheet is finer than the second outer sheet.

4. An absorbent article according to claim 1, further comprising a fluid impermeable back sheet disposed on the first outer sheet and a fluid permeable top sheet disposed on the second outer sheet with said absorbent article interposed between the back sheet and the top sheet.

* * * * *